United States Patent [19]

Wylan

[11] Patent Number: 4,726,364

[45] Date of Patent: Feb. 23, 1988

[54] ADHESIVE BANDAGE CONSTRUCTION

[76] Inventor: Peter Wylan, 2001 Mandeville Canyon Rd., Los Angeles, Calif. 90049

[21] Appl. No.: 914,888

[22] Filed: Oct. 3, 1986

[51] Int. Cl.⁴ .............................................. A61F 13/00
[52] U.S. Cl. .................................................... 128/155
[58] Field of Search ................................ 128/155, 156

[56] References Cited

U.S. PATENT DOCUMENTS

| | | | |
|---|---|---|---|
| 1,434,779 | 11/1922 | Henderson | 128/155 |
| 3,334,626 | 8/1967 | Schimmel | 128/155 X |
| 4,053,053 | 10/1977 | Tumangday | 128/155 |
| 4,121,582 | 10/1978 | Remiro | 128/157 |
| 4,133,310 | 1/1979 | Lloyd et al. | 128/156 |

*Primary Examiner*—Gregory E. McNeill
*Attorney, Agent, or Firm*—Blakely, Sokoloff, Taylor & Zafman

[57] ABSTRACT

In a preferred adhesive bandage of the type having an elongated portion having an adhesive surface on one side of the elongated portion, and a gauze portion disposed generally at the center of the adhesive surface, the improvement being a means for retaining the gauze portion in a raised position above a surface defined by the adhesive surface. The means for retaining is formed from foam material or, in an alternative embodiment partly of foam and partly of resilient plastic. Both embodiments of the means for retaining the gauze portion above the surface defined by the adhesive surface have foam ventilation members disposed in longitudinal alignment with the edges of the elongated strip.

14 Claims, 5 Drawing Figures

U.S. Patent  Feb. 23, 1988  4,726,364
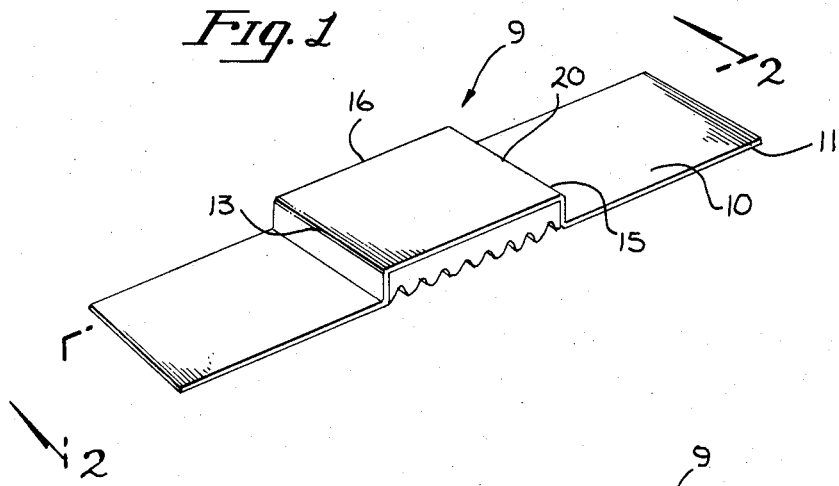
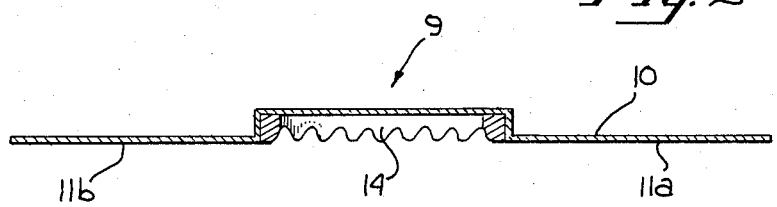
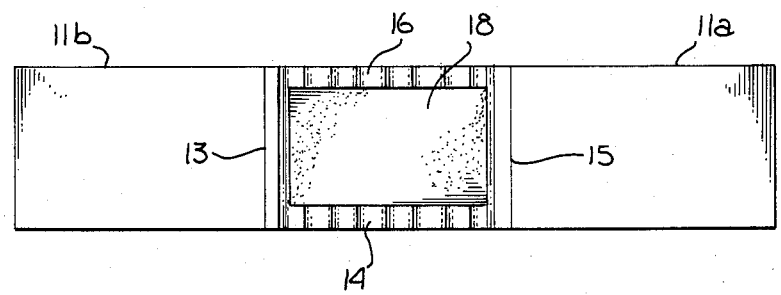
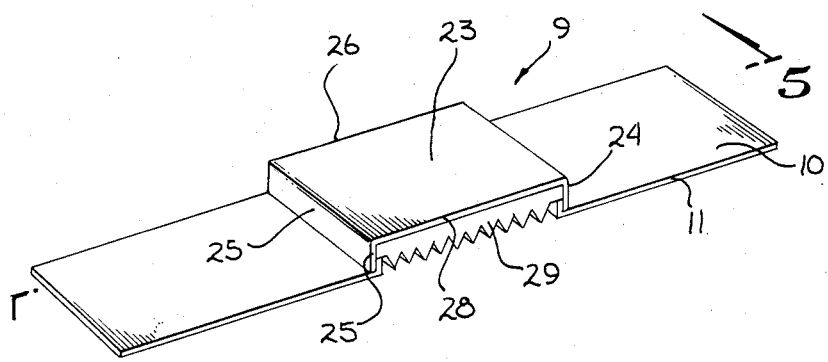
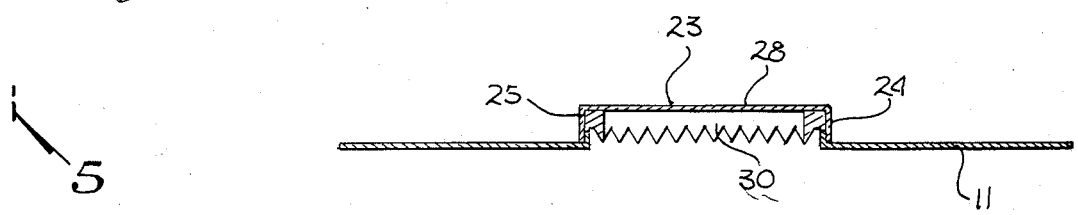

ADHESIVE BANDAGE CONSTRUCTION

THE FIELD OF THE INVENTION

The present invention relates to prepared adhesive bandages and more particularly to an improved adhesive bandage which prevents deleterious contact of the bandage with a wound being dressed, provides adequate ventilation of the wound yet, at the same time, substantially prevents passage of contaminants into the wound.

BACKGROUND OF THE PRIOR ART

Prepared bandages of various kinds are available in strip, piece or roll form. Generally, most prepared bandages consist of a strip having an adhesive surface and a gauze portion disposed in the center of the strip facing the adhesive surface. In use, the adhesive surface of the strip adheres the bandage to the skin while the gauze portion covers and protects the wound.

Many drawbacks are associated with the aforediscussed conventional prior art prepared bandages. In such prior art bandages, the central gauze portion generally comes into direct contact with the wound, thereby creating an environment wherein a scab forming on the wound often grows into or otherwise becomes attached to the gauze portion of the bandage. During removal of such prior art bandages, or when the bandages are bumped or jostled, the scab is often damaged causing a deleterious and healing-inhibiting effect upon the wound. Moreover, such prior bandages fail to provide adequate ventilation for the wound being dressed since, typically, the gauze portion of such bandages so closely overlies the wound or is adhered to it by reason of the aforementioned problem of a scab attachment to the gauze portion, that ventilation of the wound is impossible. Since a properly ventilated wound heals much faster than a nonventilated wound, the healing process of wounds dressed with such prior art bandages is greatly delayed.

Some prior art bandages have been developed in an attempt to meet some of the aforediscussed problems. U.S. Pat. No. 2,785,677 to Stumpf discloses two bandages which have, respectively, an arced member and a dome-shaped member centrally located on the adhesive portion of the bandages. The two bandages provide, respectively, a transverse arc and a dome for protection of the wound from being bumped or otherwise irritated. However, the arced shaped member of the Stumpf bandage does not substantially prevent contaminants from passing into the wound. With respect to the dome-shaped member, since when applied it entirely encloses the wound, the dome-shaped embodiment does not provide adequate ventilation to the wound. Further, the dome-shaped embodiment of Stumpf has a circular base which encloses a less than maximum surface area of the skin, thereby providing a wound with less than adequate protection. Moreover, both the arc and dome shaped members of the Stumpf bandages have sloping edges which angle upward toward the center of the portion above the wound. As such, the edges near the base of these center portions above the wound come into close and nearly overlying contact with the wound being dressed, thus presenting the aforementioned problems of having the forming scab of the wound attach to the bandage covering the wound.

SUMMARY OF THE INVENTION

The obstacles, problems, and drawbacks of the prior art are overcome in a bandage of the present invention having an elongated portion with an adhesive surface on one side of said elongated portion, and a gauze portion disposed generally at the center of said elongated portion, wherein the improvement comprises a means for retaining the gauze portion in a raised position above a surface defined by the adhesive surface. The retaining means is disposed underneath the elongated portion in substantial alignment with the gauze portion. The retaining means and the gauze portion collectively form a chamber having a predetermined width, length and height and having a substantially flat upper surface portion. The chamber has a pair of side members and a pair of transverse members which collectively define the walls of the chamber. The side members are disposed in substantial longitudinal alignment with the longitudinal edges of the elongated portion and the transverse members are disposed transversely to the side members adjacent to each end thereof. The side members each have a corrugated bottom portion for providing ventilation therethrough, wherein, when applied to a wound, the retaining means substantially prevents the wound from interacting with the gauze portion and provides ventilation of the wound while substantially preventing contaminant material from coming into contact with the wound.

The retaining means, in one embodiment, is comprised of foam material and, in another embodiment, is comprised in part of a resilient plastic frame.

BRIEF DESCRITION OF THE DRAWINGS

FIG. 1 shows a perspective view of a first embodiment of the invented bandage;

FIG. 2 shows a front elevational view of the invented bandage taken along lines 2—2 of FIG. 1;

FIG. 3 shows a bottom plan view of the invented bandage of FIGS. 2 and 1;

FIG. 4 shows a second embodiment of the invented bandage;

FIG. 5 shows a front elevational view of the invented bandage taken along lines 5—5 of FIG. 4.

DETAILED DESCRIPTION OF THE INVENTION

In FIG. 1 there is shown a perspective view of the invented bandage generally denoted by reference numeral 9 and having an elongated strip 10 which has disposed on the underside thereof an adhesive surface 11. Generally disposed at the center of elongated strip 10 and between adhesive surfaces 11a and 11b is a gauze portion 18 (shown in FIG. 3) which is retained in a raised position above a surface defined by the adhesive surface 11. Retaining means 20 and gauze portion 18 define a chamber having longitudinal side members 14 and 16 (longitudinal side member 16 not shown in FIG. 1). Longitudinal side member 16 mirrors but is otherwise identical to longitudinal side member 14, disposed in longitudinal alignment with the longitudinal edges of the elongated strip 10. Transverse members 13 and 15 are disposed, respectively, at each end of longitudinal sides 14 and 16 in transverse relationship thereto. Longitudinal side members 16 and 14 and transverse members 13 and 15 collectively define the walls of the chamber formed by retaining means 20 in which gauze portion 18 is disposed. As shown in FIGS. 1–3 the chamber formed by retaining means 20 is substantially rectangularly shaped in order to enclose a maximum amount of the surface area of the skin at the base of the chamber, thereby covering the largest possible wound size for a given bandage size. It will be appreciated that the aforementioned chamber may have a substantially rectangular or square cross sectional area.

In view of the fact that the walls 13, 14, 15 and 16 of the chamber formed by retaining means 20 are substantially orthogonal to the plane defined by the adhesive surface 11, the walls of the chamber sharply rise above and are generally orthogonal to the plane defined by adhesive surface 11, and in the same respect, the surface of the wound being dressed, thereby substantially preventing the walls or gauze 18 from interacting with the scab forming on the wound.

In the preferred embodiment, longitudinal side members 14 and 16 of retaining means 20 have corrugated bottom surfaces, which, when disposed over a wound, provide adequate ventilation for the wound while also substantially preventing particulate matter and other contaminants from coming into contact with the wound. Further, because longitudinal sides 14 and 16 are made of a foam material which allows air but not larger contaminants to pass, additional ventilation is provided. Also, in the preferred embodiment retaining means 20 is comprised of foam material, of sufficient rigidity to hold gauze material 18 above the plane defined by adhesive surface 11. However, the foam material comprising retaining means 20 is not so stiff as to be uncomfortable to a user of the invented adhesive bandage.

In FIGS. 4 and 5 there is shown another embodiment of the invented bandage wherein an alternative retaining means 23 is disclosed. FIG. 4 shows a perspective view of the second embodiment of the invented bandage while FIG. 5 shows a front elevational view thereof. As with retaining means 20 of FIGS. 1-3, retaining means 23 retains the gauze portion 18 in a raised position of the adhesive surface 11 and is partially comprised of resilient plastic material having a pliancy and flexibility sufficient to prevent the means for retaining 23 from digging into or otherwise, irritating the wound while also having a sufficient resiliency to retain the gauze portion 18 in a raised position. It will be appreciated, however, that means for retaining 23 may be comprised of other material having similar characteristics.

Retaining means 23 is comprised of longitudinal side portions 26 and 28 and transverse side portions 24 and 25. Longitudinal side portion 26 mirrors but is otherwise identical to longitudinal side portion 28. Similarly, transverse side portion 25 mirrors but is otherwise identical to transverse side portion 24. Longitudinal side portions 26 and 28 and transverse side portions 24 and 25 are comprised of resilient plastic or other similar material as previously discussed. Longitudinal side portions 26 and 28 have, respectively, foam ventilation members 29 and 30 which are disposed in longitudinal alignment with transverse side portion 26 and 28 and extend downwardly therefrom. Foam ventilation member 30 mirrors, but is otherwise identical to foam ventilation member 29. In the preferred embodiment, foam ventilation members 29 and 30 are comprised of foam material. Also, as in the first embodiment, retaining means 23 and gauze portion 18 form a chamber having walls which are generally orthogonal to the plane defined by adhesive surface 11, thereby substantially preventing the walls from interacting with the wound being dressed. As with transverse side members 16 and 14 of the first embodiment of FIGS. 1-3, foam ventilation members 29 and 30 have corrugated bottom surfaces for providing adequate ventilation of the wound being covered while substantially preventing contamination of the wound.

Also as in the first embodiment, the chamber formed by retaining means 23 has a substantially rectangular shape which encloses, at its base, a maximum amount of the surface area of the skin surrounding the wound being dressed, thereby providing the wound with a maximum amount of protection.

The above described invention may be embodied in other specific forms without departing from the spirit or essential characteristics thereof. The present embodiments are to be considered in all aspects as illustrative and unrestrictive, the scope of the invention being indicated by the appended claims rather than by the foregoing description and all changes which come within the meaning and range of equivalency are, therefor, intended to be embraced therein.

I claim:

1. An adhesive bandage of the type having an elongated portion, an adhesive surface on one side of said elongated portion, and a gauze portion disposed generally at the center of said adhesive surface wherein the improvment comprises:

a retaining means for retaining said gauze portion in a raised position above a surface defined by said adhesive surface, said retaining means being disposed underneath said elongated portion in alignment with said gauze portion, such that said retaining means and said gauze portion form a chamber of a predetermined width, length and height, said chamber having a substantially flat upper surface and also having a pair of ventilation members and a pair of transverse members, said ventilation members and said transverse members collectively defining the walls of said chamber, said ventilation members each having vent portions, said vent portions defining openings for providing adequate ventilation of said wound while also substantially preventing contamination of said wound and being disposed in substantial longitudinal alignment with the longitudinal edges of said elongated portion, said transverse members being disposed transverse to said ventilation members adjacent to each end thereof:

wherein when applied to a wound, said retaining means substantially prevents said wound from interacting with said gauze portion, permits ventilation of said wound and substantially prevents contaminant material from coming into contact with said wound.

2. The adhesive bandage as claimed in claim 1 wherein said pair of side members and said pair of transverse members are comprised substantially of foam material.

3. The adhesive bandage according to claim 1 wherein said walls are substantially orthogonal to the plane defined by said adhesive surface, thereby substantially preventing said walls from interacting with said wound.

4. The bandage as claimed in claim 1 wherein said transverse members are comprised substantially of resilient plastic material and wherein said chamber further comprises a resilient frame wherein said transverse members constitute a portion of said frame and wherein a pair of resilient members extend longitudinally from a first one of said pair of transverse members to a second one of said pair of transverse members, said resilient members being in substantial longitudinal alignment with said side members and disposed at the upper surfaces thereof, said resilient members being integral with said transverse members such that said transverse members and said resilient members define said resilient frame along the outer edged of said gauze portion.

5. The bandage according to claim 2 wherein said transverse members and said resilient members are comprised substantially of resilient plastic.

6. The bandage according to claim 1 wherein the cross-sectional area of said chamber is substantially square shaped.

7. The bandage according to claim 1 wherein said chamber is substantially rectangularly shaped area.

8. An adhesive bandage of the type having an elongated portion, an adhesive surface on one side of said elongated portion, and a gauze portion disposed generally at the center of said adhesive surface wherein the improvement comprises:

a retaining means for retaining said gauze portion in a raised position above a surface defined by said adhesive surface such that said retaining means and said gauze portion form a raised area having a substantially hollow interior, said raised area having a pair of ventilation members in longitudinal alignment with said elongated portion and a pair of transverse members juxtaposed to said ventilation member, said ventilation members each having vent openings, said vent openings being large enough to provide adequate ventilation of a wound while also substantially preventing contaminants from passing over said wound.

9. The adhesive bandage as claimed in claim 8, wherein said pair of ventilation members and said pair of transverse members are comprised substantially of foam material.

10. The adhesive bandage according to claim 8 wherein said transverse members and said ventilation members define walls of said raised area which are substantially orthogonal to the plane defined by said adhesive surface, thereby substantially preventing said walls from interacting with said wound.

11. The bandage as claimed in claim 8, wherein said transverse members are comprised substantially of resilient plastic material and wherein said retaining means further comprises a resilient frame wherein said transverse members constitute a portion of said frame and wherein a pair of resilient members extend longitudinally from a first one of said pair of transverse members to a second one of said pair of transverse members, said resilient members being in substantial longitudinal alignment with said ventilation members and disposed at the upper surfaces thereof, said resilient members being integral with said transverse members such that said transverse members and said resilient members define said resilient frame along the outer edges of said gauze portion.

12. The bandage according to claim 11 wherein said transverse members and said resilient members are comprised substantially of resilient plastic.

13. An adhesive bandage of the type having an elongated portion, an adhesive surface on one side of said elongated portion, and a gauze portion disposed generally at the center of said adhesive surface wherein the improvement comprises:

a retaining means for retaining said gauze portion in a raised position above a surface defined by said adhesive surface, said retaining means being disposed underneath said elongated portion in alignment with said gauze portion, such that said retaining means and said gauze portion form a chamber of a predetermined width, length and height, said chamber having a substantially flat upper surface and also having a pair of ventilation members and a pair of transverse members, said ventilation members and said transverse members collectively defining the walls of said chamber, said ventilation members each having a corrugated bottom surface having a corrogation sufficient to permit ventilation of said wound while substantially preventing contamination of said wound and being disposed in substantial longitudinal alignment with the longitudinal edges of said elongated portion, said transverse members being disposed transverse to said ventilation members adjacent to each end thereof;

wherein when applied to a wound, said retaining means substantially prevents said wound from interacting with said gauze portion, permits ventilation of said wound and substantially prevents contaminant material from coming into contact with said wound.

14. An adhesive bandage of the type having an elongated portion, an adhesive surface on one side of said elongated portion, and a gauze portion disposed generally at the center of said adhesive surface wherein the improvement comprises:

a retaining means for retaining said gauze portion in a raised position above a surface defined by said adhesive surface, said retaining means being disposed underneath said elongated portion in alignment with said gauze portion such that said retaining means and said gauze portion form a chamber of a predetermined width, length and height, said chamber having a substantially flat upper surface and also having a pair of ventilation members and a pair of transverse members, said ventilation members and said transverse members collectively defining the walls of said chamber, said ventilation members each being comprised of porous foam material for providing adequate ventilation of said wound and substantially preventing contamination of said wound, said ventilation members being disposed in substantial longitudinal alignment with the longitudinal edges of said elongated portion, and said transverse members being disposed transverse to said ventilation members adjacent to each end thereof, wherein when applied to a wound, said retaining means substantially prevents said wound from interacting with said gauze portion, permits ventilation of said wound and substantially prevents contaminant material from coming into contact with said wound.

* * * * *